(12) United States Patent
Pinal et al.

(10) Patent No.: US 8,104,614 B2
(45) Date of Patent: Jan. 31, 2012

(54) AUTOCLAVABLE MEDICAL INSTRUMENT CASE FOR REDUCED INSTRUMENT CORROSION

(75) Inventors: Frank Pinal, Weehawken, NJ (US); Alfred Anthony Litwak, Manasquan, NJ (US); Brian Umbach, North Caldwell, NJ (US); Akhil Kumar Singh, West New York, NJ (US)

(73) Assignee: S.S. White Technologies Inc., Piscataway, NJ (US)

( * ) Notice: Subject to any disclaimer, the term of this patent is extended or adjusted under 35 U.S.C. 154(b) by 139 days.

(21) Appl. No.: 12/771,782

(22) Filed: Apr. 30, 2010

(65) Prior Publication Data

US 2011/0266178 A1 Nov. 3, 2011

(51) Int. Cl.
*B65D 83/10* (2006.01)

(52) U.S. Cl. ...................................... 206/370; 422/300

(58) Field of Classification Search .................. 206/363, 206/369, 370, 438, 63.5; 422/299, 300, 302, 422/297; 211/70.6; 248/346.03, 346.06
See application file for complete search history.

(56) References Cited

U.S. PATENT DOCUMENTS

| | | | |
|---|---|---|---|
| 4,502,656 A * | 3/1985 | Zeitler | 248/346.03 |
| 6,217,835 B1 * | 4/2001 | Riley et al. | 422/297 |
| 7,341,148 B2 * | 3/2008 | Bettenhausen et al. | 206/370 |
| 7,544,336 B2 * | 6/2009 | Powell | 422/297 |
| 7,565,972 B2 * | 7/2009 | Steppe | 206/370 |
| 7,828,255 B2 * | 11/2010 | Yen et al. | 248/162.1 |
| 7,861,860 B2 * | 1/2011 | Bettenhausen et al. | 206/370 |
| 2006/0076254 A1 * | 4/2006 | Corbitt et al. | 206/370 |

* cited by examiner

*Primary Examiner* — Jacob K Ackun
(74) *Attorney, Agent, or Firm* — Arthur L. Lessler

(57) ABSTRACT

A case for storing medical instruments contains a rotating bracket for holding the instruments. The bracket is connected to the tray and hinged lid of the case via a movable frame, and the bracket movement is controlled by opening and closing of the lid. When the lid is closed, the bracket points the tips of the instruments downward to minimize water collection; and when the lid is opened, the instrument holding bracket rotates so that the instruments it holds are moved to a vertical position, facilitating instrument selection.

4 Claims, 5 Drawing Sheets

AUTOCLAVABLE MEDICAL INSTRUMENT CASE FOR REDUCED INSTRUMENT CORROSION

BACKGROUND OF THE INVENTION

The present invention relates to an autoclavable medical instrument case.

Most autoclavable, medical instrument cases, especially those for reusable medical instruments, are perforated on all sides to allow steam or water vapor, which is generated within an autoclave, to penetrate the case and reach the instruments within it. This process, along with the heat that helps to generate the water vapor, sterilizes both the inside of the case and the instruments.

The autoclaving of these perforated medical-instrument cases, however, results in water collecting on the tips of the instruments within the cases, causing corrosion. Although most reusable medical instruments and surgical tools are made of stainless steel, they nevertheless tend to corrode when exposed to water for prolonged periods of time. Making the situation worse, many medical instruments have custom-shaped socket-like configurations that retain water.

Accordingly, an object of the present invention is to provide an autoclavable medical instrument case that minimizes or eliminates corrosion of instruments retained within the case after autoclaving.

SUMMARY OF THE INVENTION

A case having a tray and connected lid contains at least one rotatable bracket for holding one or more medical instruments. The bracket is coupled to the lid and tray so that when the lid is closed, the bracket points the tips of instruments it holds downward to minimize water collection. When the lid is opened, the instrument holding bracket rotates to hold the instruments so that they face upward, facilitating instrument selection.

IN THE DRAWING

DETAILED DESCRIPTION

Figure 1:
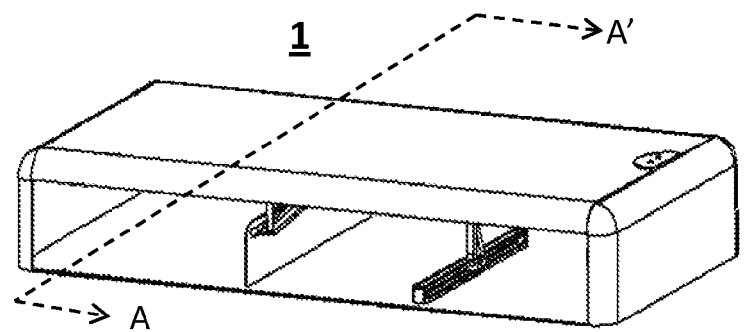
FIG. 1 is an isometric view of the case according to a preferred embodiment of the invention.

Referring to FIGS. 1 through 4, the instrument case 1 has a rectangular body and comprises: tray 2, lid 3, instrument holding bracket 4, fastening tabs 5 and 5a, movable frame 6, fastening brackets 7 and 7a, fixed frame 8, and sliding link 9.

Figure 6:
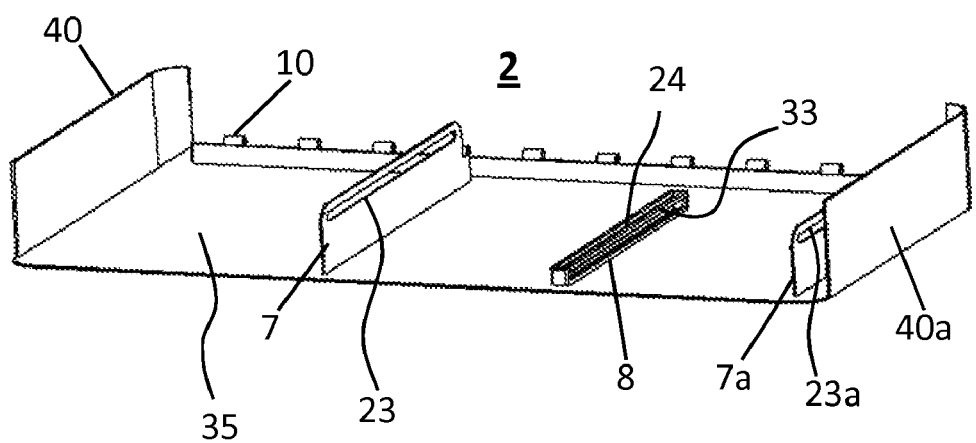
FIG. 6 is an isometric view of the tray of the case.

Referring to FIG. 6, tray 2 has a main body 35, fastening brackets 7 and 7a, and side walls 40 and 40a. The main body 35 is preferably rectangular but can alternatively be of another configuration, as long as the fastening brackets 7 and 7a, and side walls 40 and 40a are accommodated with clearance to perform their intended functions as described below, and as long as the configuration does not obstruct the movement of the lid 3, instrument holding bracket 4, movable frame 6, and sliding link 9 as described herein.

The side walls 40 and 40a (FIG. 6) are preferably rectangular, but can be of any configuration as long as they limit closure of the lid 3 and do not otherwise obstruct the movement of the lid 3, instrument holding bracket 4, movable frame 6, and sliding link 9 as described herein.

The fastening brackets 7 and 7a, (FIG. 6), fixed frame 8, and hinge 10 are fastened to the main body 35 so that their relative positions remain fixed.

Figure 2:
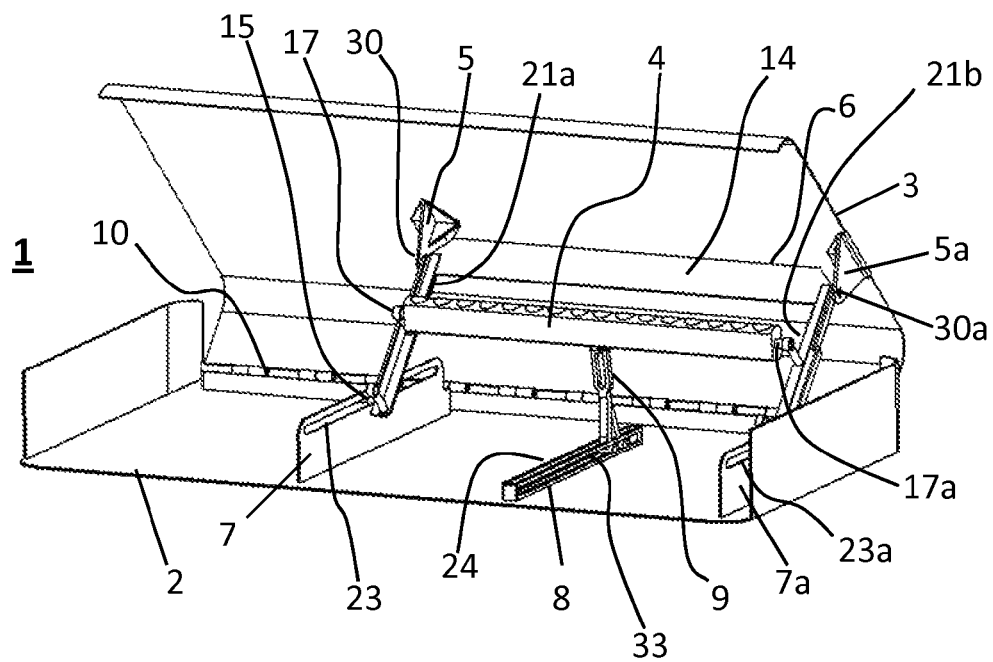
FIG. 2 is an isometric view of the case shown in FIG. 1 with the lid of the case in an open position.

The fastening brackets 7 and 7a have longitudinal slots 23 and 23a, respectively. These brackets 7 and 7a may be formed integrally with the main body 35 or secured to it, and are a fixed distance apart. They may be of any shape that accommodates the slots 23 and 23a, and allows the fastening and pivoting bosses 15 and 15a (FIG. 8) of the movable frame 6 to engage and slide along the slots 23 and 23a in cooperation with the movement of lid 3 of case 1 (FIGS. 2-4).

Figure 3:
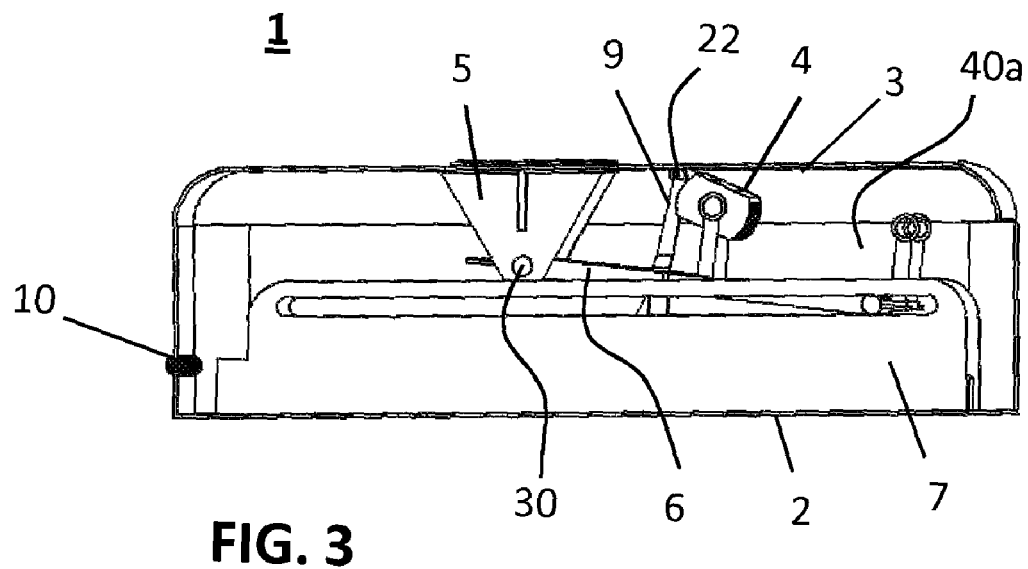
FIG. 3 is a cross-sectional view from the left side of the case with the lid in a closed position as taken from the cutting plane A-A as shown in FIG. 1.
Figure 4:
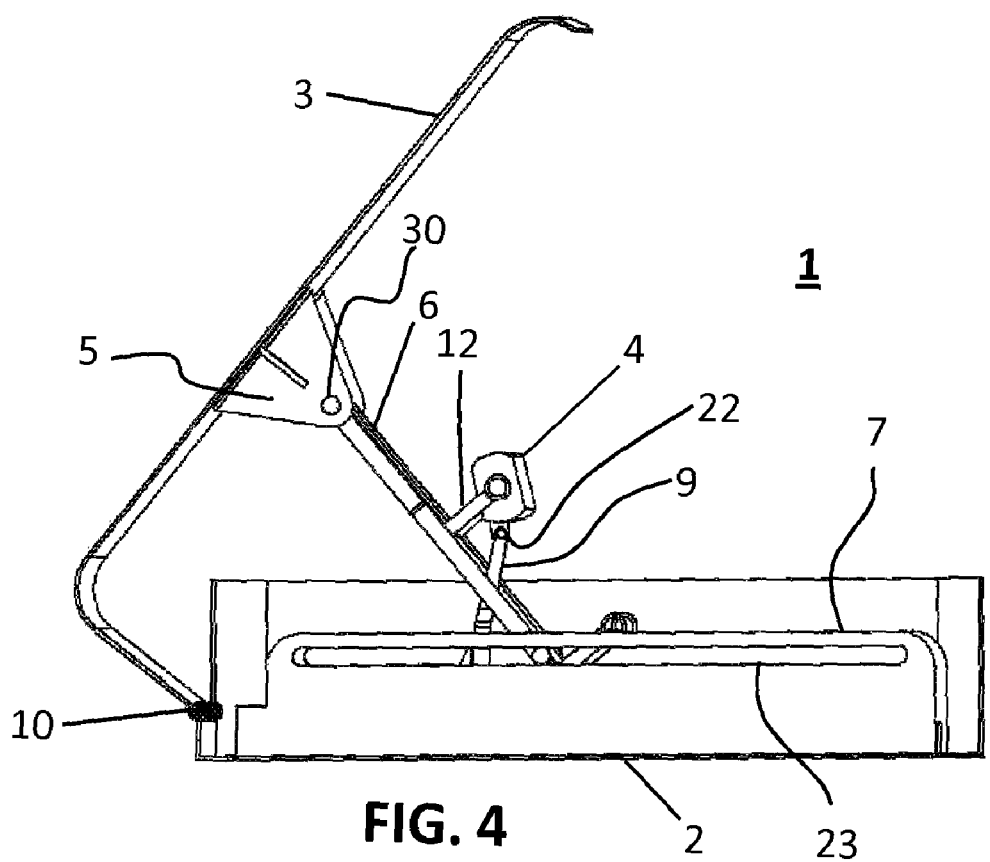
FIG. 4 is a cross-sectional view from the left side of the case with the lid in an opened position as taken from the cutting plane A-A as shown in FIG. 1.
Figure 5:
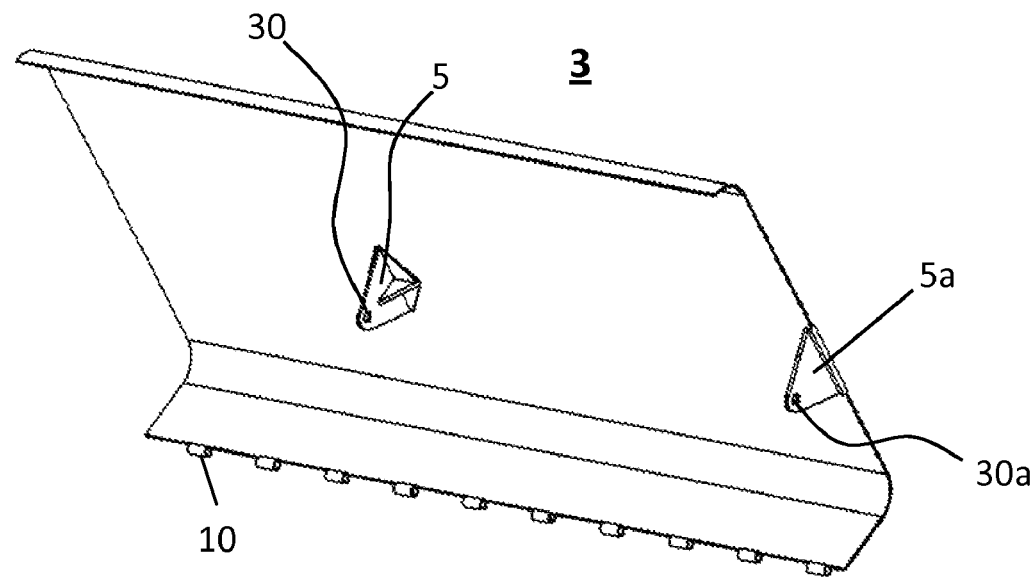
FIG. 5 is an isometric view of the lid of the case.

The fixed frame 8 (FIG. 6) of tray 2 has a main body with a fastening and sliding slot 33, and can be of any compatible configuration, and may be integral with or secured to tray 2; as long as the slot 33 allows the fastening bosses 19 and 19a (FIG. 9) of the sliding link 9 to attach and slide along slot 33 (FIG. 2) in cooperation with the movement of lid 3 of case 1 (FIGS. 3 and 4).

The tray 2 and lid 3 of case 1 (FIGS. 2-4) are fastened together by a hinge 10 that allows the lid to pivot about the hinge so that the lid may open (FIGS. 2 and 4) and close (FIGS. 1 and 3). The hinge 10 can be replaced by other fastening elements as long as they allow for pivoting motion between the lid and tray.

Figure 8:
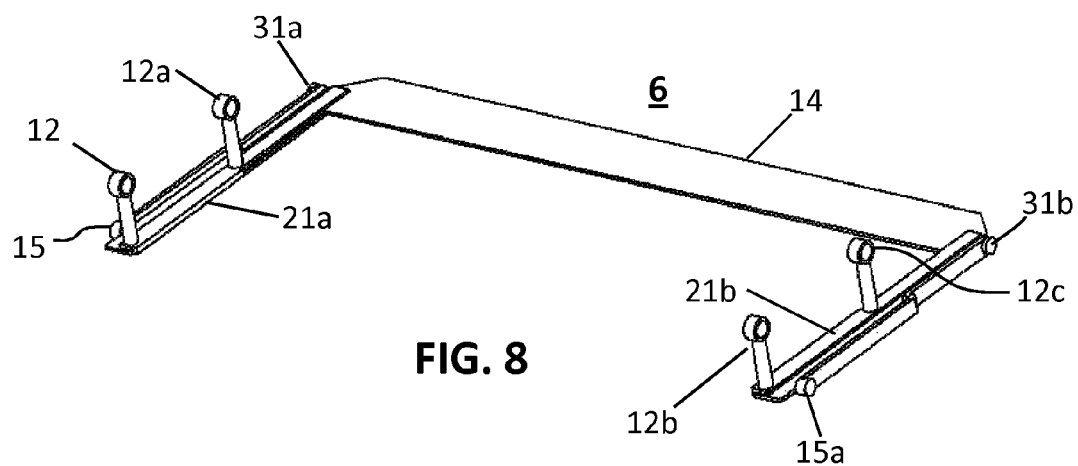
FIG. 8 is an isometric view of the moving frame element.

Referring to FIG. 8, the movable frame 6 comprises a back crosspiece 14 and parallel arms 21a, 21b that contain fastening rings 12, 12a, 12b, 12c. The back frame 14 connects the arms, causing them to move in unison. Instead of the back frame 14, the arms may be maintained in parallel relationship by separate mechanisms. The frame 14 may be of any configuration that does not interfere with the motion of the sliding link 9 and the instrument holding bracket 4 as the lid 3 is opened and closed (FIGS. 2-4). The arms 21a, 21b can also be of any configuration as long as they do not interfere with the opening and closing of the lid 3 and allow the fastening rings 12a, 12c and bosses 15, 15a to attach to their mating pegs 17, 17a and slots 23a, 23b respectively.

In addition, the shape and configuration of the arms 21a, 21b should not obstruct, but should facilitate the motion of the fastening rings and bosses with respect to the mating pegs and slots.

Figure 9:
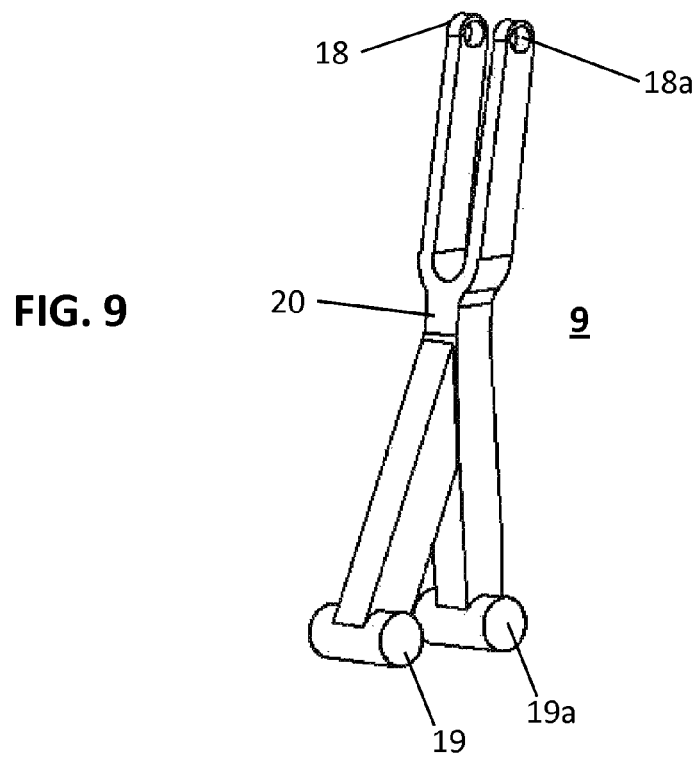
FIG. 9 is an isometric view of the sliding element.

The fastening rings 12, 12a, 12b, 12c and bosses 15, 15a on the movable frame 6 (FIG. 8) allow the pegs 17, 17a on the instrument holding bracket 4 (FIGS. 7a, 7b) to engage the frame 6 and pivot about the rings 12a, 12c as the frame 6 moves from closed position shown in FIG. 3 to the open position shown in FIG. 4. The movable frame 6 moves with movement of the lid 3 and the sliding link 9 (FIG. 9).

The bosses 31a, 31b on the movable frame 6 engage and pivot about the holes 30a, 30b of the lid tabs 5, 5a to coordinate movement of the frame 6 and instrument holding bracket 4 with the opening and closing of the lid 3 (FIGS. 3-4).

The bosses 15, 15a of the frame 6 allow it to attach to, pivot about, and slide forward and back by engagement of the bosses with the slots 23, 23a in the brackets 7, 7a of the tray 2; which movement is designed so as to not obstruct the motion of the movable frame 6 and to coordinate with the motion of lid 3 as it is opened and closed (FIGS. 3-4).

Referring to FIG. 4, when the lid 3 is moved from the closed to the open position, the frame 6 is caused to move toward the back of the case 1 and to pivot into the diagonal position shown.

Referring to FIG. 9, the sliding link 9 has a main body 20, upper fastening rings 18, 18a, and lower fastening bosses 19, 19a. While one sliding link is preferred, more than one can be used for improved stability.

The main body 20 is elongated but may be of another configuration as long as it does not obstruct the motion of the instrument holding bracket 4. The upper fastening rings 18, 18a engage the pegs 32, 32a of the downwardly extending tab 22 of the instrument holding bracket 4 (FIG. 7b) and allow the instrument holding bracket 4 to pivot so as to essentially control its orientation when the lid is moved between the closed and open positions thereof.

The lower fastening bosses 19, 19a (FIG. 9) of sliding link 9 engage the sliding slots 33 fixed frame 8 (FIG. 6), and the sliding-link slot 24 (FIG. 6) allows the body 20 of the sliding link 9 to pass through the fixed frame 8 vertically while lower fastening bosses 19, 19a (FIG. 9) of the sliding link 9 engage the sliding slots 33 of the fixed frame 8; together these mating conditions allow the link 9 to slide from the front to the back of the tray 2 while remaining essentially vertically positioned (FIGS. 2 to 4).

Figure 7A:
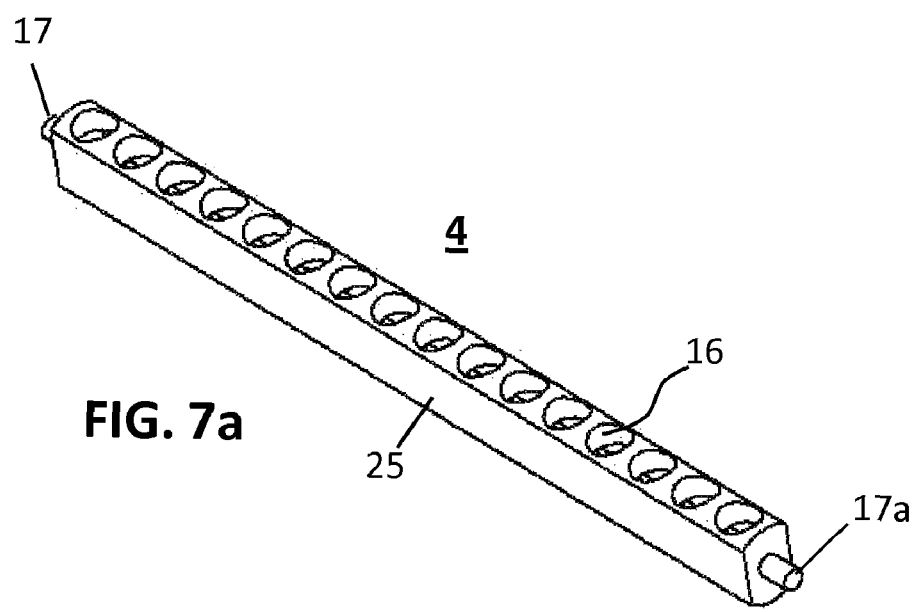
FIG. 7a is an isometric view of the instrument holding bracket.
Figure 7B:
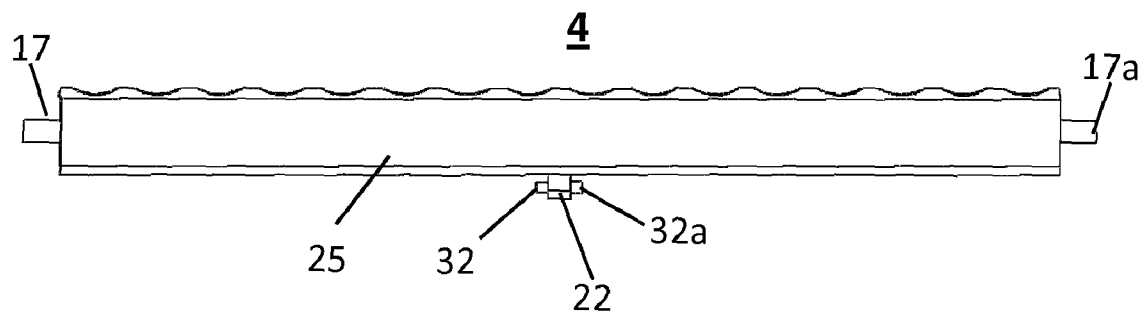
FIG. 7b is a front view of the instrument holding bracket showing the fastening and pivoting feature.

Referring to FIGS. 7a and 7b, the instrument holding bracket 4 has a main body 25 with instrument insertion holes 16 and laterally extending pegs 17, 17a. The main body 25 has an elongated rectangular prism shape, but can alternatively have any configuration that facilitates the holding of the medical instruments to be autoclaved; as long as it does not obstruct the motion of the movable frame 6, sliding link 9, and lid 3. The instrument insertion holes 16 can have regular and irregular shapes, but circular-shaped holes are preferred.

The instrument holding bracket 4 moves in synchronism with the movement of the movable frame 6, since it is operatively engaged therewith. The engagement of the pegs 32, 32a of the bracket 4 with the holes 18, 18a of the sliding link 9 allows the bracket 4 to pivot as the lid 3 of the case 1 is opened and closed, in synchronism with the motion of both the moving frame 6 and the sliding link 9.

The following pairs of coupled elements can be of any configuration, and the male and female members thereof may be interchanged, as long as the members of each pair mechanically complement each other and allow the associated parts of the case to move as previously described: (i) slots 23, 23a and bosses 15, 15a; (ii) holes 30, 30a and bosses 31a, 31b; (iii) rings 12a, 12c and pegs 17, 17a, or rings 12, 12b and pegs 17, 17a; (iv) pgs 32, 32a and rings 18, 18a; and (v) bosses 19, 19a and slot 33. Additional fastening elements, such as a pins, screws and bolts, rivets, etc., may be employed to facilitate both the fastening of said coupled elements to each other and previously described component movements, without impairing either.

With the case 1 construction described above, as the lid 3 is opened, the movable frame 6 is pulled into a diagonal position and moves toward the back of the case 1, and synchronously, the instrument holding bracket 4 moves toward the back of the case 1 and slightly up, causing the sliding link 9 to also move toward the back of the case.

As the instrument holding bracket 4 moves toward the back of the case, its slight upward motion causes the link 9 to apply a downward force to the bracket tab 22, causing the bracket 4 to rotate from a downward angled position as shown in FIG. 3—wherein the instrument receiving holes 16 are oriented downward to minimize water retention—to an upward angled position as shown in FIG. 4 wherein said holes can receive or make instruments more easily accessible for removal.

Conversely, when the lid 3 is closed, the downward and forward motion of the instrument holding bracket 4, caused by the downward and forward motion of the movable frame 6, causes the rings 18, 18a of the sliding link 9 to impart an upward force to the bracket tab 22. This upward force causes the bracket 4 to rotate from the vertically-oriented position shown in FIG. 4 to the downward-oriented position shown in FIG. 3.

We claim:

1. A case for holding medical instruments, comprising:
   a tray;
   a lid rotatably connected to the tray adjacent an edge thereof;
   a movable frame interconnected with the lid and the tray in such a way that the frame moves with respect to the tray as the lid is opened and closed, the frame having substantially parallel arms;
   an instrument holding bracket for receiving one or more instruments, said bracket being supported by and rotatably coupled to said arms; and
   a sliding link coupled to said instrument holding bracket and tray in such a way that when the lid is open any instruments received by said instrument holding bracket are oriented upward, and as the lid is closed the link causes the instrument holding bracket to rotate to a position wherein such instruments are oriented downward to minimize retention of water on tips thereof.

2. The case according to claim 1, further comprising a slotted fixed frame secured to said tray, wherein said link has a lower end slidably engaged with the slot of the fixed frame.

3. An instrument case for holding elongated medical instruments having tips, comprising:
   a tray;
   a lid hinged to the tray at the rear edge thereof;
   a pair of substantially parallel arms operatively associated with the lid and tray in such a way that the arms move toward the front edge and major surface of the tray as the lid is closed, and in the opposite direction as the lid is opened; and
   an instrument holding bracket rotatably mounted to the arms and operatively associated with the tray in such a way that when the lid is closed the tips of such instruments point toward the tray major surface, and when the lid is opened the tips point away from that surface.

4. A case for holding medical instruments, comprising:
   a tray;
   a lid connected to the tray;
   an instrument holding bracket for receiving one or more instruments; and
   coupling means operatively associated with the lid and tray for (i) when the lid is in an open position, orienting the bracket so as to retain instruments with their tips or ends pointing upward, and (ii) rotating the bracket to a second position when the lid is closed, to retain instruments with their tips or ends pointing downward.

* * * * *